(12) United States Patent
Sjölund

(10) Patent No.: US 11,179,134 B2
(45) Date of Patent: Nov. 23, 2021

(54) METHOD AND SYSTEM FOR CALIBRATION

(71) Applicant: ELEKTA AB (PUBL), Stockholm (SE)

(72) Inventor: Jens Sjölund, Stockholm (SE)

(73) Assignee: ELEKTA AB (PUBL), Stockholm (SE)

( * ) Notice: Subject to any disclaimer, the term of this patent is extended or adjusted under 35 U.S.C. 154(b) by 959 days.

(21) Appl. No.: 15/302,414

(22) PCT Filed: Apr. 15, 2014

(86) PCT No.: PCT/EP2014/057659
§ 371 (c)(1),
(2) Date: Oct. 6, 2016

(87) PCT Pub. No.: WO2015/158372
PCT Pub. Date: Oct. 22, 2015

(65) Prior Publication Data
US 2017/0027540 A1 Feb. 2, 2017

(51) Int. Cl.
*A61B 6/00* (2006.01)
*A61B 6/03* (2006.01)
*A61N 5/10* (2006.01)

(52) U.S. Cl.
CPC .............. *A61B 6/583* (2013.01); *A61B 6/032* (2013.01); *A61B 6/50* (2013.01); *A61N 5/1039* (2013.01);
(Continued)

(58) Field of Classification Search
None
See application file for complete search history.

(56) References Cited

U.S. PATENT DOCUMENTS

| | | | |
|---|---|---|---|
| 2005/0117708 A1* | 6/2005 | Cho | A61B 6/027 378/164 |
| 2008/0232664 A1 | 9/2008 | Nagamine et al. | |

(Continued)

FOREIGN PATENT DOCUMENTS

| | | |
|---|---|---|
| JP | 2006-51216 A | 2/2006 |
| JP | 2008-228966 A | 10/2008 |

(Continued)

OTHER PUBLICATIONS

English translation of Japanese Office Action dated Apr. 4, 2018, for Application No. 2016-562872.
(Continued)

*Primary Examiner* — Christopher Koharski
*Assistant Examiner* — Younhee Choi
(74) *Attorney, Agent, or Firm* — Birch, Stewart, Kolasch & Birch, LLP

(57) ABSTRACT

A method of calibrating a positioning system in a radiation therapy system which includes a radiation therapy unit having a fixed radiation focus, includes irradiating a calibration tool having at least one reference object, capturing at least one two-dimensional image including cross-sectional representations of reference objects of the calibration tool and determining image coordinates of the representation of each reference object. Based on the reference objects' image coordinates, positions of the reference objects in the stereotactic coordinate system relative to an origin of the calibration tool and the position of the origin of the calibration tool relative to the imaging unit, a position difference between the position of the calibration tool in the stereotactic coordinate system and a position of the calibration tool in an imaging system coordinate system including a translational and rotational position difference is calculated.

20 Claims, 8 Drawing Sheets

(52) U.S. Cl.
CPC .... *A61N 5/1075* (2013.01); *A61N 2005/1061* (2013.01); *A61N 2005/1076* (2013.01)

(56) References Cited

U.S. PATENT DOCUMENTS

2009/0285366 A1* 11/2009 Essenreiter .......... A61B 6/4441
378/207
2013/0229495 A1    9/2013 Bani-Hashemi et al.
2015/0087881 A1    3/2015 Miyamoto et al.

FOREIGN PATENT DOCUMENTS

JP      2013-192702 A     9/2013
WO     WO 2012/146301 A1   11/2012
WO     WO-2012146301 A1 * 11/2012   ........... A61N 5/1075

OTHER PUBLICATIONS

Forster et al., "Stereotactic Radiosurgery," Surgery, No. 97, Oct. 1, 1991, pp. 2323-2325, XP000228581.

* cited by examiner

Out-of-plane rotations

In-plane rotation

Detector plane

METHOD AND SYSTEM FOR CALIBRATION

FIELD OF THE INVENTION

The present invention relates to the field of radiation therapy. In particular, the present invention concerns a method of calibrating a positioning system in a radiation therapy system comprising a radiation therapy unit having a fixed radiation focus.

BACKGROUND OF THE INVENTION

The development of surgical techniques has made great progress over the years. For instance, for patients requiring brain surgery, non-invasive surgery is now available which is afflicted with very little trauma to the patient.

One system for non-invasive surgery is sold under the name of Leksell Gamma Knife®, which provides such surgery by means of gamma radiation. The radiation is emitted from a large number of fixed radioactive sources and is focused by means of collimators, i.e. passages or channels for obtaining a beam of limited cross section, towards a defined target or treatment volume. Each of the sources provides a dose of gamma radiation which is insufficient to damage intervening tissue. However, tissue destruction occurs where the radiation beams from all radiation sources intersect or converge, causing the radiation to reach tissue-destructive levels. The point of convergence is hereinafter referred to as the "focus".

A patient to be treated with radiation therapy is fixated to a positioning system using a stereotactic fixation unit. Hence, the stereotactic fixation unit immobilizes a treatment volume in the patient in relation to the positioning system, i.e. immobilizes a portion of the patient containing a tissue area to be treated. For example, when the treatment area or volume is a portion of tissue within the head of a patient, the stereotactic fixation unit generally constitutes a head fixation frame which, for example, may be fixed to the skull of the patient, e.g. by fixation screws or the like. Then, the coordinates of the stereotactic fixation unit is defined by a stereotactic fixation unit coordinate system, which through the fixed relationship with the treatment volume also is used for defining the outlines of the treatment volume. In operation, the stereotactic fixation unit, and hence the stereotactic fixation unit coordinate system, is moved in relation to the fixed radiation focus such that the focus is accurately positioned in the intended coordinate of the fixation unit coordinate system.

Examples of such a stereotactic fixation unit and coordinate system include the Leksell stereotactic head frame and the Leksell XYZ coordinate system, respectively. The Leksell XYZ coordinate system is a Cartesian coordinate system defined by three orthogonal axes perfectly aligned with the frame of a stereotactic fixation unit, which is arranged with three orthogonal sides. In relation to a patient, the x-axis extends in the medial-lateral direction of the patient, the y-axis extends in the anterior-posterior direction, and the z-axis extends in the cranial-caudal direction.

In other words, if a patient is properly positioned in the Leksell XYZ coordinate system, the x-axis would run from ear to ear, the z-axis from head to toe, and the y-axis from back to front of the patient.

In connection with radiation therapy in radiation therapy systems, the therapy is planned in a treatment planning system. The treatment volume of the patient is scanned using an imaging system, for example, a cone beam computed tomography (CBCT) system and the scanned images are input to the treatment planning system. Computed tomography (CT) imaging, also referred to as a computed axial tomography (CAT) scan, involves the use of rotating x-ray equipment, combined with a digital computer, to obtain images of the body. Using CT imaging, cross sectional images of body organs and tissues can be produced. Using CT imaging, not only can physicians confirm that tumors exist, but they can also pinpoint their locations, accurately measure the size of tumors, and determine whether or not they've spread to neighboring tissues. In addition to the diagnosis of certain cancers, CT imaging is used for planning and administering radiation cancer treatments, as well as for planning certain types of surgeries. Using CBCT images a volumetric reconstruction of the treatment volume can be created, which can be used in planning the treatment. To this end, the volumetric reconstruction of the treatment volume must be exactly related to the focus position of the radiation therapy system and the positioning system.

However, the CBCT reconstruction is made with relation to the rotation axis of the imaging system and the rotation axis of the CBCT system and the stereotactic fixation unit coordinate system are not aligned but will have variation due to, for example, manufacturing tolerances. Such angular variations between the CBCT coordinate system and the stereotactic fixation unit coordinate system can, for example, lead to positioning errors when the patient is fixated to the positioning system and positioned within the radiation unit for a therapy session.

In the prior art, there have been attempts to solve the above-mentioned problems. In WO 2012/146301 by the same applicant, systems and methods for calibrating an imaging system are presented. According to WO 2012/146301, a three-dimensional reconstruction of a calibration tool is created based on sets of images and the three-dimensional reconstructions is then compared to the known position and orientation, i.e. pose, of the calibration tool in the stereotactic coordinate system to obtain a position difference. This solution requires that a large number of images are captured in order to create an adequate volumetric reconstruction of the calibration tool.

Similar problems with misalignments between objects are also dealt with in technical fields such as computer vision and robotics. In these fields, common tasks also include to identify specific objects in images and to determine each object's position and orientation relative to a coordinate system. For example, machine learning algorithms are used to learn the mappings from 2D image features to pose transformation based on a large set of training cases or try to optimize the fit through a feedback mechanism. Another approach is so called geometric methods where sets of control points on an object, typically corners or other characterizing features, are identified in images of the object and based on this the pose transformation can be solved. This approach requires that the image sensor (camera) is calibrated and the mapping from 3D points in the scene and the 2D points in the image are known. However, these methods are not adapted for use in medical systems.

Thus, there is still a need of improved methods and systems for determining and compensating for deviations between a coordinate system of an imaging system, such as a CBCT system, and the stereotactic fixation unit coordinate system. There is also a need for methods and systems for determining and compensating for deviations between a coordinate system of an imaging system, such as a CBCT system, and the stereotactic fixation unit coordinate system with an improved accuracy and, thus, an improved and more accurate calibration.

SUMMARY OF THE INVENTION

An object of the present invention is to provide systems and methods for compensating for deviations between a coordinate system of an imaging system, such as a CBCT system, and a stereotactic fixation unit coordinate system.

An object is also to provide methods and systems for determining and compensating for deviations between a coordinate system of an imaging system, such as a CBCT system, and the stereotactic fixation unit coordinate system with an improved accuracy and, thus, an improved and more accurate calibration.

These and other objects are achieved by providing a calibration method having the features defined in the independent claim. Preferred embodiments are defined in the dependent claims.

In the context of the present application, the term "pose" defines the combination of position and orientation of an object.

According to an aspect of the present invention, there is provided a method for calibrating an imaging system for capturing images of a patient in relation to a radiation therapy system. The radiation therapy system comprises a radiation therapy unit having a fixed radiation focus and a positioning system for positioning a patient in relation to the fixed focus in the radiation therapy unit. According this aspect of the present invention, the method includes irradiating a calibration tool comprising at least one reference object with ionizing radiation during an image scanning procedure using a radiation unit of the imaging system. The calibration tool, or a reference point of the calibration tool, and the at least one reference object have known positions or coordinates in the stereotactic coordinate system. Further, at least one two-dimensional image including cross-sectional representations of reference objects of the calibration tool is captured during the image scanning procedure using a detector of the imaging system. Image coordinates of the representation of each reference object in the captured image are determined and a position of the origin of the calibration tool relative to the imaging unit is determined. Based on the reference objects image coordinates, positions of the reference objects in the stereotactic coordinate system relative to an origin of the calibration tool and the position of the origin of the calibration tool relative to the imaging unit, a transformation between the position of the calibration tool in the stereotactic coordinate system and a position of the calibration tool in an imaging system coordinate system is calculated. In other words, based on the reference objects image coordinates, pose of respective reference object in the stereotactic coordinate system relative to an origin of the calibration tool and the position of the origin of the calibration tool relative to the imaging unit, a transformation between the pose of the calibration tool in the stereotactic coordinate system and a pose of the calibration tool in an imaging system coordinate system is calculated According to another aspect of the present invention, there is provided a system for calibrating an imaging system for capturing images of a patient in relation to a radiation therapy system comprising a radiation therapy unit having a fixed radiation focus and a positioning system for positioning a patient in relation to the fixed focus in the radiation therapy unit. The imaging system is configured to irradiate a calibration tool comprising at least one reference object with ionizing radiation during an image scanning procedure using a radiation unit, The calibration tool, or a reference point of the calibration tool, and the at least one reference object have known positions or coordinates in the stereotactic coordinate system. The imaging system is further configured to capture at least one two-dimensional image including cross-sectional representations of reference objects of the calibration tool using a detector during the image scanning procedure. A processing unit is configured to determine image coordinates of the representation of each reference object in the captured images and obtain a position of the origin of the calibration tool relative to the imaging unit. Further, the processing unit is configured to calculate a transformation between the position of the calibration tool in the stereotactic coordinate system and a position of the calibration tool in an imaging system coordinate system based on the reference objects image coordinates, positions of the reference objects in the stereotactic coordinate system relative to an origin of the calibration tool and the position of the origin of the calibration tool relative to the imaging unit. In other words, based on the reference objects image coordinates, pose of respective reference object in the stereotactic coordinate system relative to an origin of the calibration tool and the position of the origin of the calibration tool relative to the imaging unit, a transformation between the pose of the calibration tool in the stereotactic coordinate system and a pose of the calibration tool in an imaging system coordinate system is calculated.

The transformation includes a translational and rotational position difference between the position of the calibration tool in the stereotactic coordinate system and a position of the calibration tool in an imaging system coordinate system.

The present invention can be used in radiation therapy systems such as in a LINAC system or a Leksell Gamma Knife® system.

The present invention is based on the insight that there are angular variations or deviations between a coordinate system of an imaging system, such as a CBCT system, and the stereotactic coordinate system that defines the treatment positions due to, for example, manufacturing tolerances. The CBCT system is used to capture images of the patient and the treatment volume and the reconstructed image of the treatment volume must therefore relate to the focus of the therapy unit and the patient positioning system. The CBCT coordinates are physically offset from the focus and it is not possible to mechanically know from tolerances what position the CBCT system has in relation to the focus. Thus, these variations or deviations cause positioning errors when the patient is translated into the radiation therapy unit for a treatment. Even a very small sinusoidal error may result in large deviations if the patient is translated a large distance and may hence cause large positioning errors. These insights have led to the invention and the idea of determining and compensating for the deviations between a coordinate system of the imaging system, such as a CBCT system, and the stereotactic coordinate system that defined the treatment positions. Using the determined deviation, the position and rotation of the reconstructed object can be determined in relation to the stereotactic coordinate system.

In order to determine the deviation, a calibration tool that easily can be aligned and positioned exactly in the stereotactic coordinate system and thereby securely be kept still during image acquisition is used. For example, the calibration tool can be mounted or attached to a stereotactic fixation unit of the patient positioning system. The stereotactic fixation unit for immobilizing a treatment volume is in fixed engagement with the patient positioning system and cannot be translated or rotated in relation to the positioning system.

The position of the calibration tool in a coordinate system related to the imaging system is determined using at least one two-dimensional image captured by means of the detector of the imaging system. In preferred embodiments of the present invention, a calibration tool having at least three ball bars attachable to the fixation unit is used. Each ball bar has a known position (coordinates) in the stereotactic coordinate system and relative to an origin of the calibration tool. Due to the size, shape and material of the reference objects of the calibration tool, their projections will occupy regions in the images having a high contrast against the background and with no overlap, either horizontally or vertically. Thus, the projections of the respective reference objects can be identified and their image coordinates can be determined. Since the coordinates of the reference objects in the stereotactic coordinate system are known and the position of the detector in the imaging system, the image coordinates of the reference objects can be determined.

By determining the vectors from a point of the X-ray source of the imaging system to respective reference object of the reference tool for each image, the position or coordinates of the calibration tool can be determined with respect to the imaging system coordinate system. Thereafter, a transformation between the determined position of the calibration tool in the imaging system coordinate system and the known position of the calibration tool in the stereotactic fixation unit coordinate system can be calculated.

The present invention provides a very accurate calibration in comparison to prior art technologies.

According to embodiments of the present invention, the position of the origin of the calibration tool relative to the imaging unit is calculated. In alternative embodiments, the position of the origin of the calibration tool relative to the imaging unit is predetermined and known.

According to embodiments of the present invention, positions of the reference objects relative to the imaging unit is determined based on the reference objects image coordinates and a position of the detector relative to the imaging unit and the transformation is calculated based on positions of the reference objects relative to the imaging unit, the positions of the reference objects in the imaging coordinate system and positions of the calibration tool relative to the imaging unit.

According to embodiments of the present invention, the calculation of the transformation is further based on a distance between the imaging unit and the detector and a detector rotation. That is, a position difference of the detector or a transformation between the position of the detector in the stereotactic coordinate system and a position of the detector in the imaging system coordinate system.

According to embodiments of the present invention, the vectors between the reference objects positions and the position of the imaging unit are determined based on the respective reference objects image coordinates and an assumption that the vectors between the reference objects positions and the position of the imaging unit are parallel, for respective reference objects, with vectors between positions of the reference objects image coordinates and the imaging unit. The relation between the vectors between the reference objects positions and the position of the imaging unit and the vectors between positions the reference objects image coordinates and the imaging unit is then used in calculating the transformation.

According to embodiments of the present invention, the relation between the vectors for the reference objects image coordinates relative to the imaging unit and the vectors of the reference objects positions relative to the imaging unit is defined as a scalar and a value of the scalar is determined based on the positions of the reference objects relative to the imaging unit, the positions of the reference objects in the imaging coordinate system and positions of the calibration tool relative to the imaging unit.

According to embodiments of the present invention, the positions of the reference objects relative to the origin of the calibration tool in the imaging system coordinate system is calculated based on the positions of the reference objects relative to the origin of the calibration tool in the stereotactic coordinate system and the transformation is calculated based on the reference objects image coordinates, the coordinates of the reference objects in the imaging coordinate system and coordinates of the calibration tool relative to the imaging unit.

According to embodiments of the present invention, each relation between a position of a reference object in the stereotactic coordinate system and a position of that reference object in the imaging coordinate system is calculated as a vector defining a translational and rotational position difference using a vector rotation method.

According to embodiments of the present invention, the calibration tool comprises: attachment means for enabling releasable attachment to the fixation arrangement of the patient positioning system; and reference objects having a shape enabling a position determination in six dimensions. In embodiments of the present invention, the calibration tool comprises at least three reference objects each including a rod attached to a base plate comprising the attachment means and a steel ball attached to respective rod.

According to embodiments of the present invention, a calibration of the imaging system is performed including determining a rotational axis of the imaging system. This calibration step may be performed before a session to determine the deviation between the imaging system coordinate system and the stereotactic coordinate system is performed.

As readily understood by the person skilled in the art, various known methods for determining the radiation focus could be used, of which some have been described above. However, the present invention is not restricted to the particular examples shown and described herein, but any suitable measurement method for determining the radiation focus is contemplated within the scope of the present invention.

BRIEF DESCRIPTION OF THE DRAWINGS

Preferred embodiments of the invention will now be described in greater detail with reference to the accompanying drawings, in which FIG. 1 schematically illustrates the general principle of a radiation therapy system suitable for calibration using the present invention.

DESCRIPTION OF PREFERRED EMBODIMENTS

Figure 1:
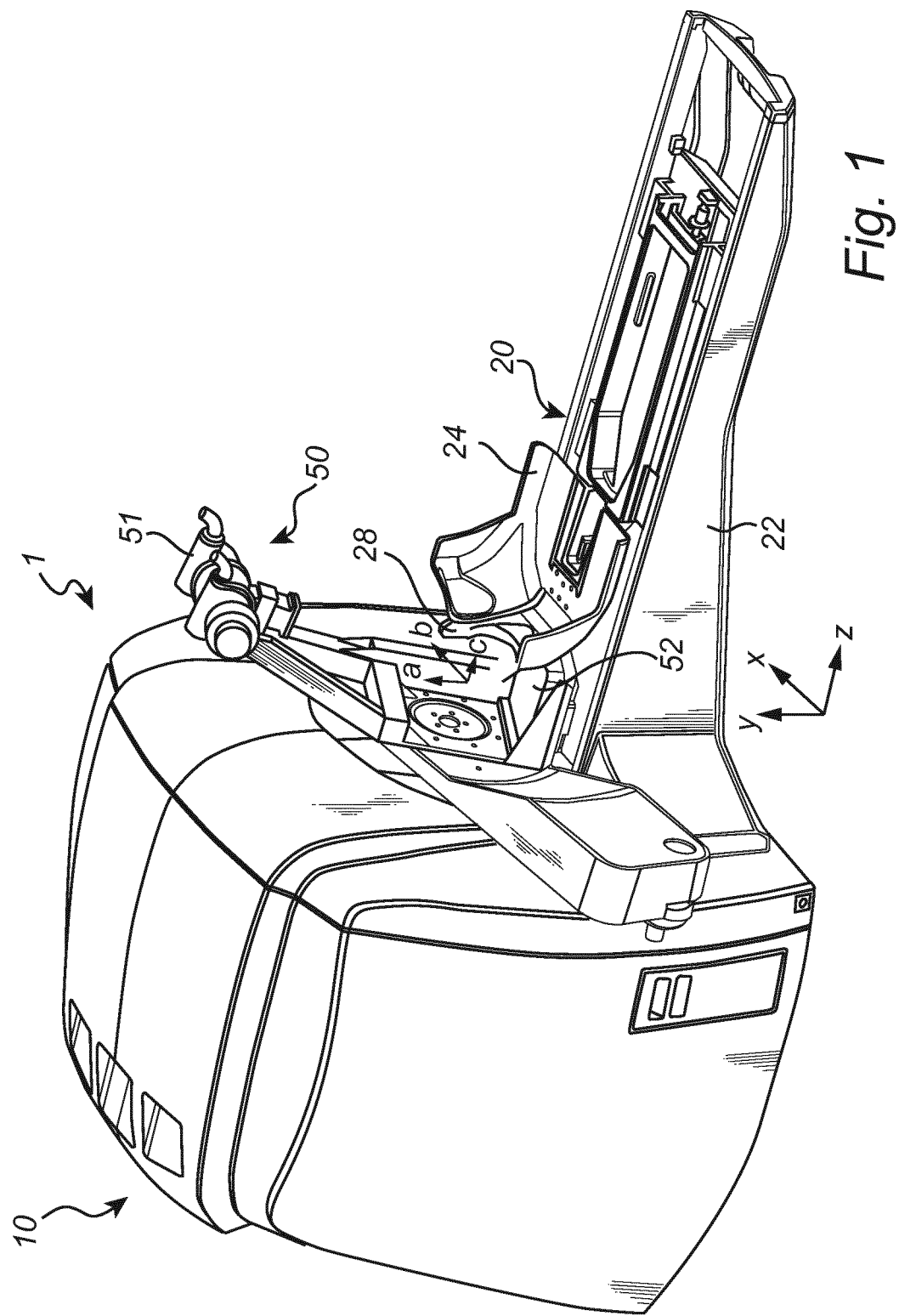

With reference to FIG. 1, a radiation therapy system 1 for which the present invention is applicable comprises a radiation unit 10 and a patient positioning unit 20. In the radiation unit 10, there are provided radioactive sources, radioactive source holders, a collimator body, and external shielding elements. The collimator body comprises a large number of collimator channels directed towards a common focus, in a manner as is commonly known in the art.

The collimator body also acts as a radiation shield preventing radiation from reaching the patient other than through the collimator channels. Examples of collimator arrangements in radiation therapy systems applicable to the present invention can be found in WO 2004/06269 A1, which is hereby incorporated by reference.

The patient positioning unit 20 comprises a rigid framework 22, a slidable or movable carriage 24, and motors (not shown) for moving the carriage 24 in relation to the framework 22. The carriage 24 is further provided with a patient bed (not shown) for carrying and moving the entire patient. At one end of the carriage 24, there is provided a fixation arrangement 28 for receiving and fixing a stereotactic fixation unit (not show), either directly or via an adapter unit (not shown), and thereby preventing the stereotactic fixation unit from translational or rotational movement in relation to the movable carriage 24. The patient can be translated using the patient positioning unit 20 in the coordinate system of the radiation therapy system 1 or the patient positioning unit 20, along at least in the three orthogonal axes x, y, and z shown in FIG. 1. The patient can, in some embodiments, also be translated along, for example, a rotational axis.

An imaging system 50 for capturing images of a patient, for example, in connection with treatment planning or treatment is arranged or located at the radiation unit 10, for example, a cone beam computed tomography (CBCT) system.

The imaging system 50 includes an X-ray source 51 and a detector 52. The X-ray source 51 and detector 52 are arranged to rotate around a rotation axis c (see FIG. 1) of a coordinate system (a, b, c) of the imaging system 50 to capture images of a patient located on the patient bed 26 at different angles. Ideally, the X-ray source 51 and the detector 52 rotate around the z-axis of the patient positioning unit 20, which is aligned with the rotation axis c of the imaging system 50. However, in practice, there are, for example, alignments errors due manufacturing tolerances leading to a misalignment between the coordinate system of the patient positioning unit 20 and the imaging system 50 and accordingly the c-axis is not aligned with the z-axis.

In computed tomography, a three-dimensional image is generated by rotating the imaging system around the object in very small steps (e.g. <1°) around a single axis of rotation while taking a series of two-dimensional X-ray images. In other applications, the object is rotated around the imaging in small steps. Normally, the imaging device or the object is rotated, for example, 180° or 360° around the object or imaging device, respectively. Afterwards, a final three-dimensional image can be numerically reconstructed based on the two-dimensional images and can be displayed either as a series of sectional images or a three-dimensional image.

As can be understood from FIG. 1, the described embodiment concerns a radiation therapy system for providing gamma radiation therapy to a target volume in the head of human patient. Such therapy is often referred to as stereotactic surgery. During therapy, the patient head is fixed in a stereotactic fixation unit, for example, using a bite-block and a fixation unit in the form of a stereotactic head frame, which comprises engagement points adapted for engagement with the fixation arrangement 28 of the radiation therapy system. Thus, during the stereotactic surgery, the head of the patient is fixed in the stereotactic frame, which in turn is fixedly attached to the patient positioning system via the fixation arrangement 28. During movement of the treatment volume in the head of the patient in relation to the radiation focus, e.g. along the three axes x, y, and z shown in FIG. 1, the entire patient is moved. Thus, there is no relative to movement between the head frame and the carriage 24 of the patient positioning system 20.

Figure 2:
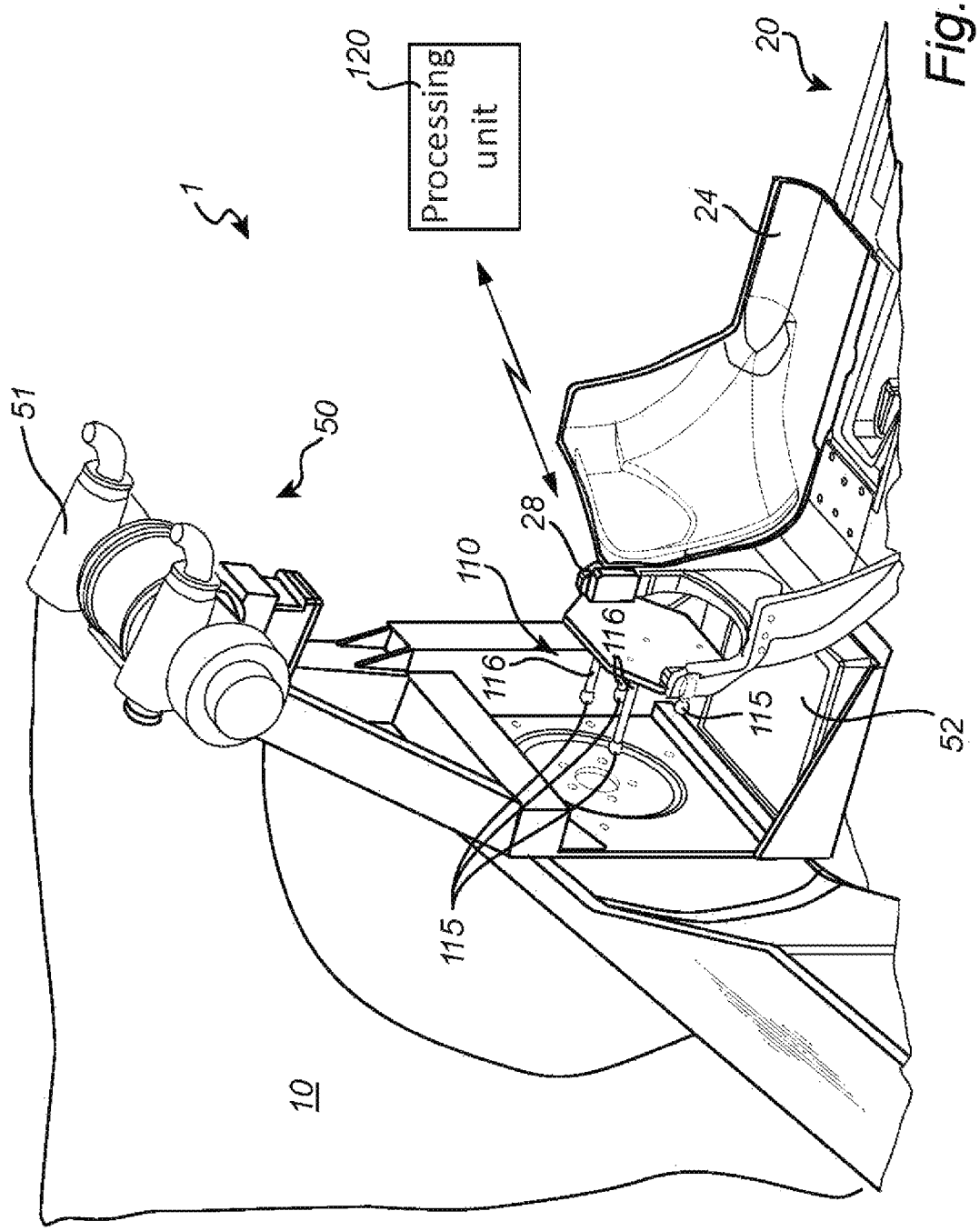
FIG. 2 schematically illustrates an embodiment of the system according to present invention implemented in the radiation therapy system of FIG. 1.
Figure 3:
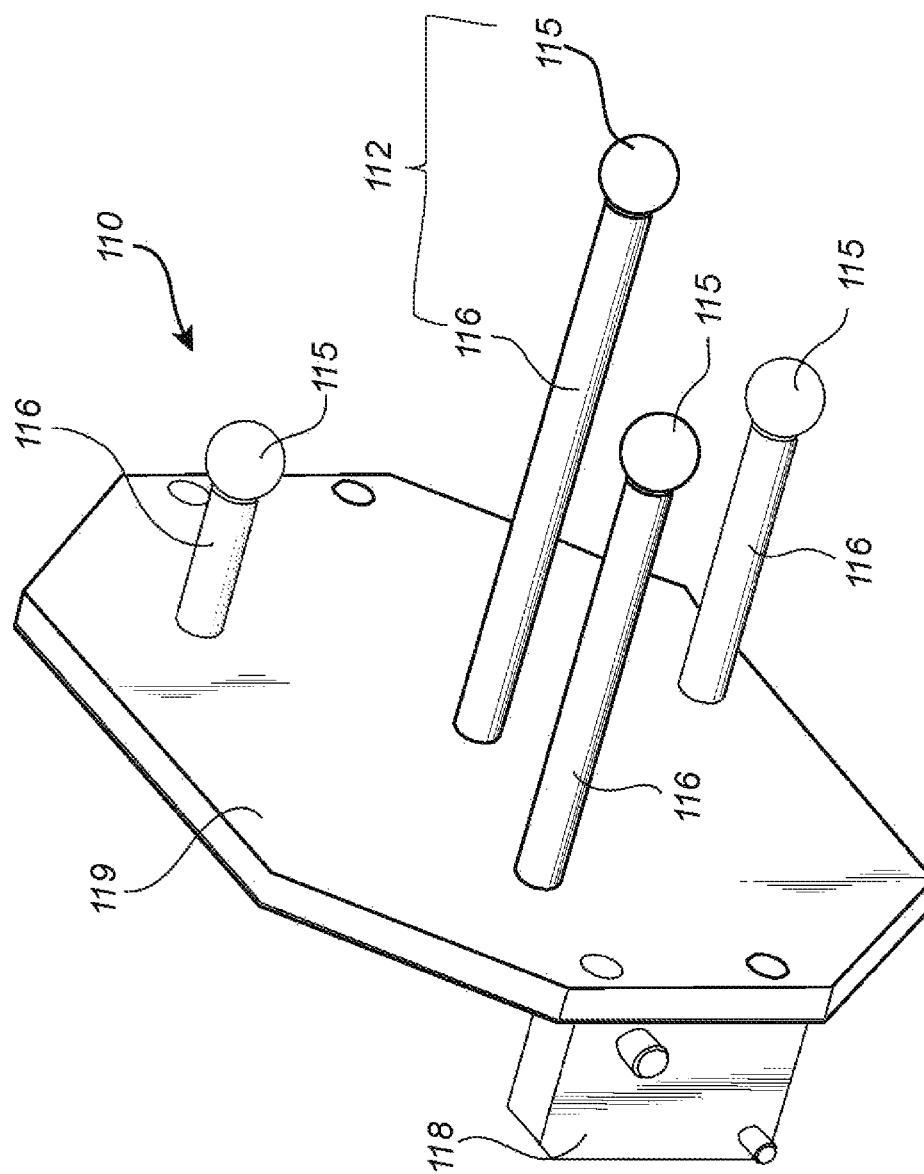
FIG. 3 schematically illustrates an embodiment of the calibration tool according to the present invention.

Turning now to FIG. 2, an embodiment of the system according to the present invention will be discussed. In FIG. 2, the system 1 according to the present invention is schematically shown together with a schematically illustrated radiation unit 10 and an imaging system 50. The system 1 according to the present invention comprises on the general level a calibration tool 110 arranged to be releasably and firmly attached to the fixation arrangement 28 of the radiation therapy system and processing unit 120, for example, a personal computer (PC). In FIG. 3, a more detailed view of an embodiment of the calibration tool 110 is shown.

The calibration tool 110 is arranged to be easily aligned and positioned exactly in the stereotactic fixation unit coordinate system. By attaching the calibration tool 110 firmly by means of attachment means 118 without any possibility to movement of the calibration tool 110 relative to the patient positioning unit 20, it can be secured that the calibration tool is located at a defined and predetermined position, $x_{cal.tool}$, $y_{cal.tool}$, and $z_{cal.tool}$, in the stereotactic fixation unit coordinate system and that it is kept still during image acquisition.

Preferably, the calibration tool 110 comprises at least one reference object or mark 112 having predetermined or known positions, respectively, in the stereotactic fixation unit coordinate system when the tool 110 is attached to the fixation arrangement 28. That is, positions of the reference objects or marks 112 relative to the predetermined position of the calibration tool 110 are known and thus have predetermined coordinates in the stereotactic fixation unit coordinate system. The reference objects 112 are made of a material and are arranged and shaped such that they can be identified in the two-dimensional images captured by the detector 52 of the imaging system 50.

In the embodiment of the calibration tool 110 shown in FIGS. 2 and 3, the calibration tool 110 comprises four reference objects 112 each including a rod 116 provided with a steel ball 115 attached on a plate 119. Each reference object 112 has a predetermined position in the stereotactic fixation unit coordinate system when the calibration tool 110 is attached to the fixation arrangement 28.

In order to allow an identification of the reference objects in the two-dimensional images captured by the detector 52, the reference objects 112 are made of a material that attenuates the X-ray radiation emanating from the imagining unit or X-ray source 51 such as steel. The X-rays are attenuated by the reference objects 112 which entails that a representation of each reference object is captured by the detector and that a representation, as a shadow, can be seen in each image. The procedure for identifying each reference object representation will be described below.

A processing unit 120 is connectable to the imaging system 50 such two-way communications is allowed, for example, wirelessly using, for example, Bluetooth or WLAN. Thereby, the processing unit 120 may, for example, obtain image information from the imaging system 50 and send instructions to imaging system 50 to initiate an image scanning procedure.

On a general level, the processing unit 120 is configured to calculate a transformation or a translational and rotational position difference between the position of the calibration tool 110 in the stereotactic coordinate system and a position of the calibration tool 110 in the imaging system coordinate system. The coordinate system of the stereotactic fixation unit (as defined by the axes x, y, and z) in which the calibration tool 110 is positioned is not aligned with the coordinate system of the imaging system (defined by the axes a, b, and c) due to, for example, manufacturing tolerances.

Thus, the processing unit 120 determines the position, $a_{cal.tool}$, $b_{cal.tool}$, and $c_{cal.tool}$, of the calibration tool 110 in the coordinate system of the imaging system 50 or rather the positions of the reference objects, i.e. a set of coordinates is obtained where each reference object is associated with three coordinates. Preferably, the coordinates of each reference object 114 are determined resulting in an array of position coordinates.

Furthermore, the processing unit 120 is configured to calculate a transformation between the determined position of the calibration tool in the coordinate system related to the imaging system, $a_{cal.tool}$, $b_{cal.tool}$, and $c_{cal.tool}$, and a position of the calibration tool in the stereotactic fixation unit coordinate system, $x_{cal.tool}$, $y_{cal.tool}$, and $z_{cal.tool}$, to determine a relationship between the coordinate system related to the imaging system and the position of the calibration tool in the stereotactic fixation unit coordinate system. Preferably, the transformation between the known positions of the reference marks in the stereotactic fixation unit coordinate system and the determined positions of the calibration tool in the coordinate system related to the imaging system are determined.

The calculation is based on the reference objects image coordinates $d_{xy}$, positions $r_{ob}$ of the reference objects 112 in the stereotactic coordinate system relative to an origin, o, of the calibration tool 110 and a position $r_{so}$ of the origin, o, of the calibration tool 110 relative to the imaging unit 51.

In embodiments of the present invention, the calculation of the transformation is based positions $r_{sd}$ of the reference objects relative to the imaging unit 51, the positions $r_{o'b'}$ of the reference objects in the imaging coordinate system and positions $r_{so}$ of the calibration tool relative to the imaging unit 51.

Figure 6:
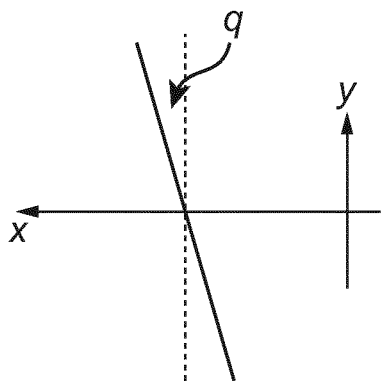
FIG. 6 illustrates detector rotation compared to the stereotactic coordinate system.
Figure 6:
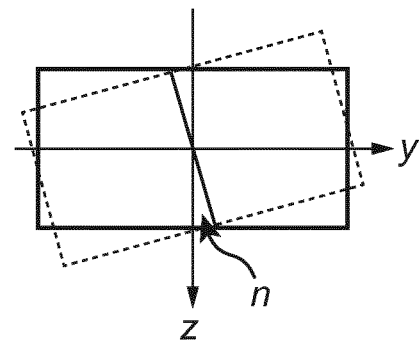
Figure 6:
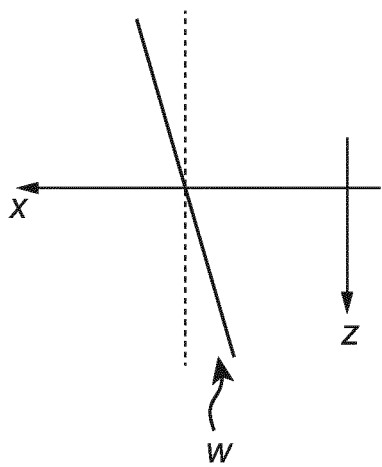
Figure 6:
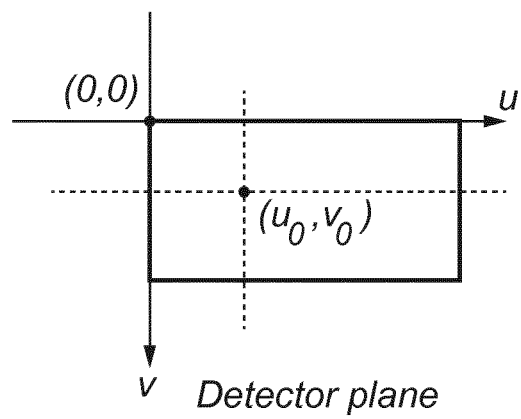

In embodiments of the present invention, the calculation of the transformation is further based on a distance SDD (see FIG. 4) between the imaging unit 51 and the detector 52 and a detector rotation between a position of the detector in the stereotactic coordinate system and a position of the detector in the imaging unit coordinate system. With reference to FIG. 6, the vector rotation is defined in three parameters, where q and w are out-of-plane rotation angles and n is the in-plane rotation angle. The detector plane is aligned such that the v axis is parallel to the z axis and the u axis is parallel to the y axis. The rotation angle of the detector plane along the axis of $u=u_0$ is q, the rotation angle of the detector plane along the axis of $v=v_0$ is w, and the rotation angle of the detector plane along the point of $(u_0, v_0)$ is n. The axis x, y, z relate to the stereotactic coordinate system (see FIG. 1) and u and v relate to the detector plane.

In embodiments of the present invention, vectors $r_{sb}$ between the reference objects positions and the position of the imaging unit 51 is determined based on the respective reference objects image coordinates $d_{xy}$ and an assumption that the vectors $r_{sb}$ between the reference objects positions and the position of the imaging unit 51 are parallel, for respective reference objects 112, with vectors $r_{sd}$ between positions the reference objects image coordinates $d_{xy}$ and the imaging unit 51 and using the relation between the vectors $r_{sd}$ between the reference objects positions and the position of the imaging unit 51 and the vectors $r_{sb}$ between positions the reference objects image coordinates $d_{xy}$ and the imaging unit 51 in calculating the transformation.

According to embodiments of the present invention, positions $r_{o'b'}$ of the reference objects 112 relative to the origin o of the calibration tool 110 in the imaging system coordinate system is calculated based on the positions $r_{ob}$ of the reference objects relative to the origin o of the calibration tool 110 in the stereotactic coordinate system and the transformation is calculated based on the reference objects image coordinates $d_{xy}$, the coordinates $r_{o'b'}$ of the reference objects in the imaging coordinate system and coordinates $r_{so}$ of the calibration tool relative to the imaging unit 51.

Figure 4:
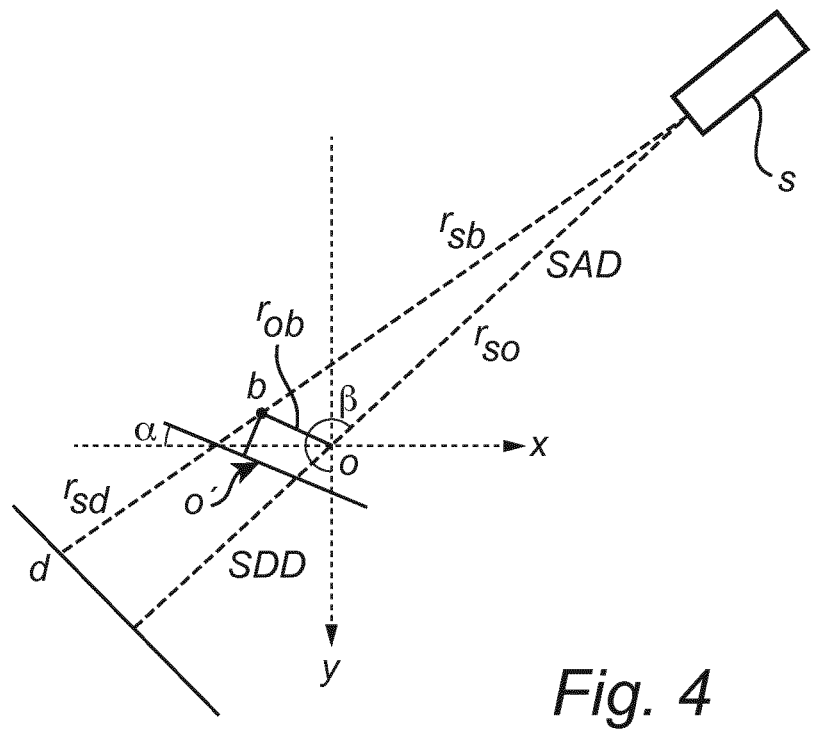
FIG. 4 schematically illustrates the geometry seen from the front of the radiation unit of FIG. 1 in a counter-direction to the direction of the z-axis of the stereotactic coordinate system.
Figure 5:
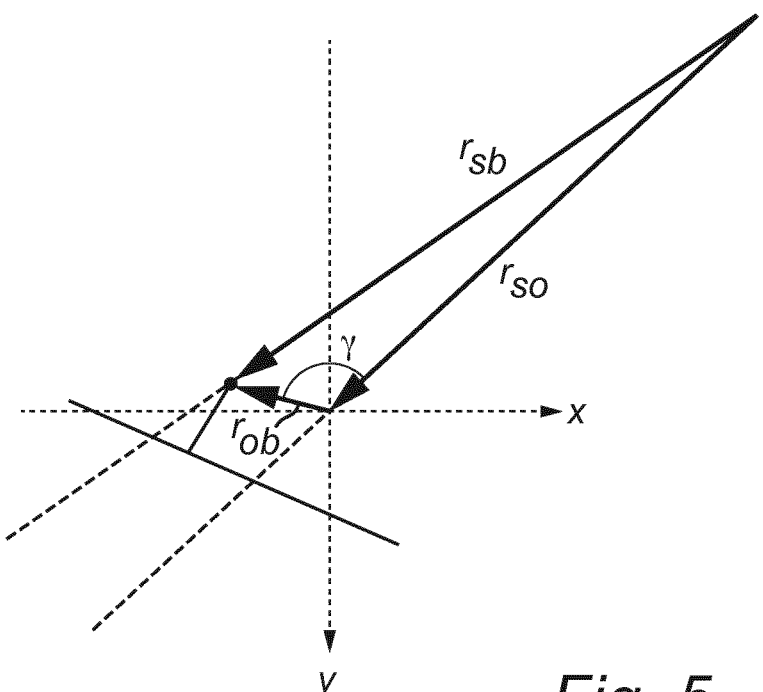
FIG. 5 schematically illustrates an enlarged view of the geometry seen from the front of the radiation unit of FIG. 1 in a counter-direction to the direction of the z-axis.
Figure 7:
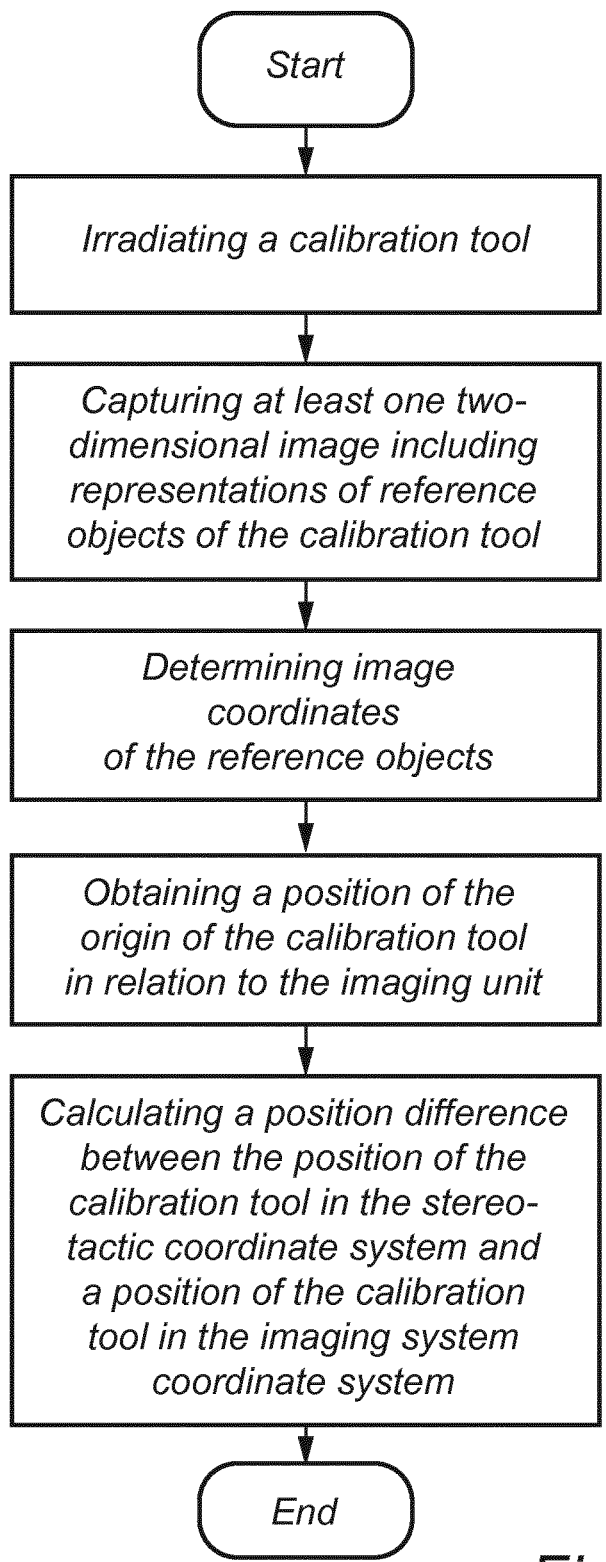
FIG. 7 is a flow chart illustrating the overall steps of the method according to the present invention.
Figure 8:
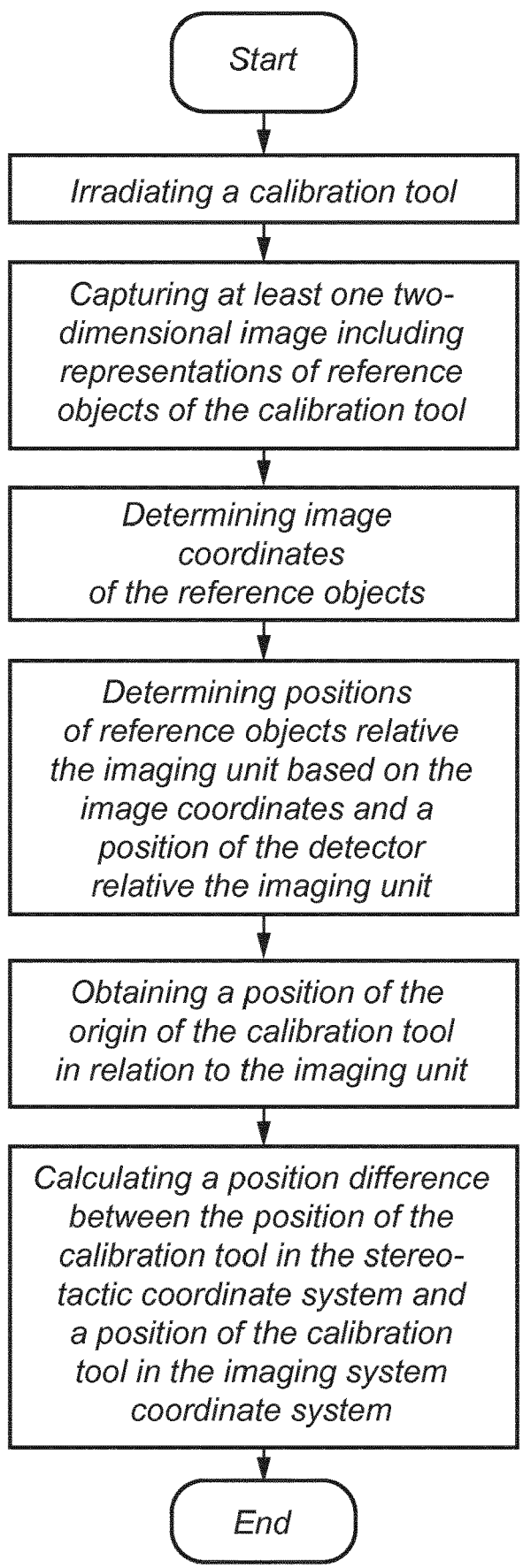
FIG. 8 is a flow chart illustrating the steps of the method according to an embodiment of the present invention.
Figure 9:
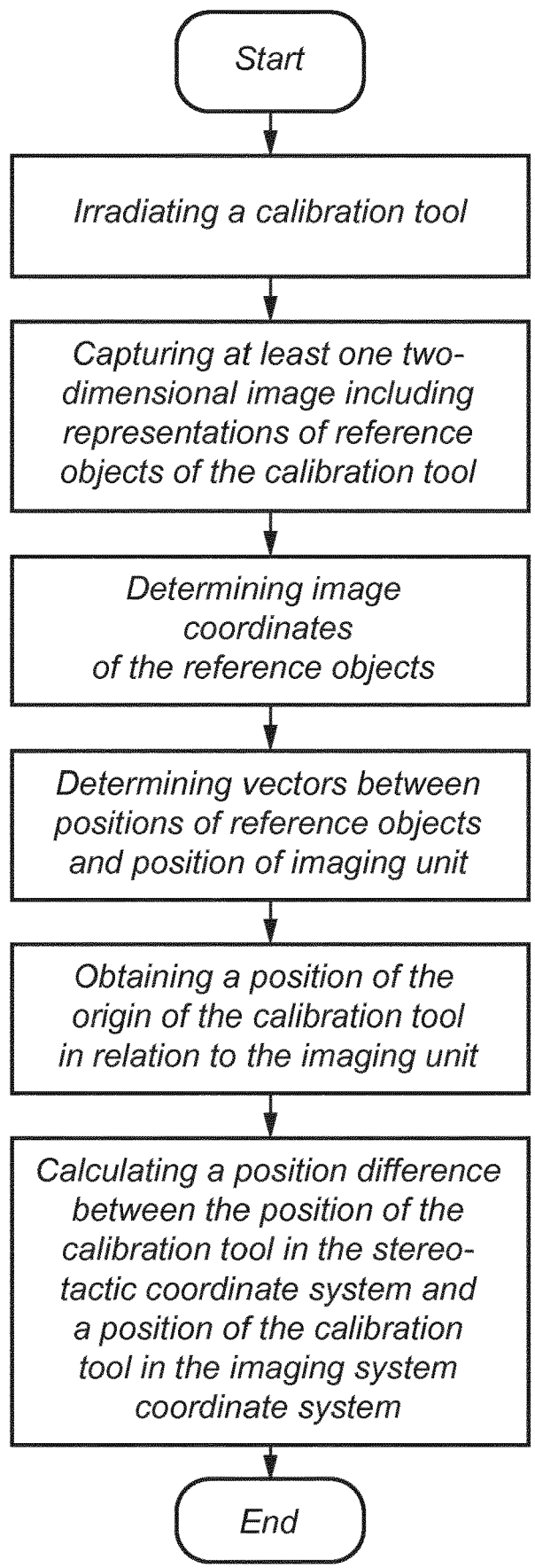
FIG. 9 is a flow chart illustrating the steps of the method according to an embodiment of the present invention.

With reference now to FIGS. 4-9, the method according to the present invention for calibrating an imaging system 50 for capturing images of a patient in connection with treatment planning or treatment in a radiation therapy system will be described. The method may, for example, be performed in a system as described in FIG. 2. FIGS. 4-6 schematically show geometries during the imaging procedure and FIGS. 7-9 show flow charts of embodiments of the method according to the present invention.

With reference to FIGS. 4 and 5, the geometry is schematically illustrated seen from front of the radiation unit 10, in this embodiment a Gamma knife, i.e. in a counter-direction to the direction of the z-axis of the stereotactic coordinate system shown in FIG. 1. The X-ray source 51, at position s (i.e. at coordinates $a_s$, $b_s$, $c_s$ of the imaging system coordinate system), emits radiation which is attenuated by a reference object 112, at position b (i.e. at coordinates $x_b$, $y_b$, $z_b$ in the stereotactic coordinate system). A clearly distinguishable shadow can then be detected on the detector 52 at position d ($d_x$, $d_y$). Based on the images, the position of the representation of each reference object, d, in space, i.e. $x_d$, $y_d$, $z_d$ in the stereotactic coordinate system. The calibration tool 110 is located at point o, i.e. a reference point of the calibration tool 110 is located at point $x_o$, $y_o$, $z_o$ in the stereotactic coordinate system. The position of the calibration tool 110 in the imaging system 50 is o', i.e. $a_{o'}$, $b_{o'}$, $c_{o'}$.

The vector $r_{sb}$ is the vector from point s to point b, i.e. the vector from the X-ray source 51 to respective reference object 112. The vector $r_{ob}$ is the vector from point o to point b, i.e. the vector from the center point of the calibration tool 110 to respective reference object 112. This vector $r_{ob}$ is known. The vector $r_{so}$ is the vector from point s to point o, i.e. the vector from the X-ray source 51 to the calibration tool 110. The vector $r_o$. SDD is the "Source to Detector Distance", i.e. the distance between the X-ray source 51 to the detector 52.

The gantry angle, β, defines the angle between a current position, s, of the X-ray source 51 and the y-axis. The angle α defines the rotation for which correction is required, thus, the position, o', of the calibration tool 110 in the coordinate system of the imaging system 50 and compared to the position, o, of the calibration tool 110 in the stereotactic coordinate system. FIG. 5 is a more detailed view of the geometry shown in FIG. 4.

With reference to FIG. 4, the vector $r_{sb}$ can be expressed as:

$$r_{sb} = r_{so} + r_{ob} = r_{so} + r_{oo'} + r_{o'b} \quad (1)$$

where the notation $r_{sb}$, as mentioned above, denotes the vector from point s (the X-ray source 51) to point b (the respective reference object 112). It is assumed that the position of the reference objects 112 relative to the center point, o, of the calibration tool 110 is known. The relation between the coordinates in the stereotactic coordinate system and the coordinates in the rotated coordinate system, i.e. the coordinate system of the imaging system, can be determined by using an algorithm for vector rotation in space, for example, Rodrigues rotation formula, given an axis $\hat{k}$ and an angle of rotation $\alpha$:

$$R(r,\hat{k},\alpha) = r\cos\alpha + (\hat{k} \times r)\sin\alpha + \hat{k}(\hat{k} \cdot r)(1-\cos\alpha) \quad (2)$$

Since the rotation axis is a unit vector it can be expressed with two parameters, $\theta$ and $\phi$, as $$\hat{k}(\theta,\phi) = (\cos\phi\sin\theta, \sin\phi\sin\theta, \cos\theta) \quad (3)$$

The gantry rotation is taken into account. Assuming a static frame of reference as defined in FIG. 4 this can be done by applying equation (2) with $\hat{k} = \hat{z}$ and $\alpha = \beta$ to $r_{so}(\beta=0)$ and $r_{sd}(\beta=0)$:

$$r_{so} = R(r_{so}(\beta=0),\hat{z},\beta) = (y_s\sin\beta - x_s\cos\beta, -y_s\cos\beta - x_s\sin\beta, -z_s) \quad (4)$$

$$r_{sd} = R(r_{sd}(\beta=0),\hat{z},\beta) = (x_d\cos\beta - y_d\sin\beta, y_d\cos\beta + x_d\sin\beta, z_d) \quad (5)$$

The vector $r_{sd} = (x_d, y_d, z_d)$ can be calculated from the images for example by center of mass calculation. Each representation of a reference object 112 will occupy a region on the detector surface (i.e. in the image) larger than a pixel. According to embodiments of the present invention, one point or pixel, in on the detector surface is selected for each reference object that accurately represents its projection. Based on the selected points $d_x$ and $d_y$ on the detector surface, the vector $r_{sd}$ ($x_d$, $y_d$, $z_d$) can be determined. The reference objects 112 have a high contrast against the background and thresholding is therefore an efficient method for identifying or determining the projections. The calibration tool 110 and the reference objects 112 are preferably designed such that no overlaps, either horizontally or vertically, between different projections arise in the images. According to preferred embodiments, a region of interest is determined for each projection and the point that is determined to accurately represent the projection is selected from that region of interest, for example, using a center of mass calculation.

Since the vector $r_{sb}$ is parallel with $r_{sd}$ the following applies: where $\lambda$ is a scalar. The value of this scalar can be extressed by applying the cosine formula to the triangle shown in FIG. 5 which yields:

$$\|r_{sb}\|^2 = \|r_{sb}\|^2 + \|r_{sb}\|^2 - 2\|r_{sb}\|\|r_{sb}\|\cos\gamma \quad (7)$$

Combining equation (7) with equation (6) and expressing the lengths as scalar products yields the following:

$$\lambda = \frac{1}{\|r_{sd}\|}\sqrt{r_{so} \cdot r_{so} + r_{ob} \cdot r_{ob} + 2r_{so} \cdot r_{ob}} \quad (8)$$

$$\lambda = \frac{\|r_{so} + r_{ob}\|}{\|r_{sd}\|} \quad (9)$$

Based on equations (8) and (9), equation (1) can be expressed as:

$$\frac{r_{sd}}{\|r_{sd}\|} = \frac{r_{so} + r_{oo'} + r_{o'b}}{\|r_{so} + r_{oo'} + r_{o'b}\|} \quad (10)$$

The degrees of freedom are the translation $r_{oo'} = (x_0, y_0, z_0)$ and the rotation, determined by $\theta$, $\phi$, $\alpha$, of the calibration tool and the source-to-axis distance (SAD). Equation (10) is solved for each reference object in each image. In preferred embodiments, three reference objects are used and 300 images are captured during an imaging session. Further, equation (10) may, according to preferred embodiments, be solved numerically, in a least-squares sense.

Below, an example of a numerical solution of equation (10) employing the Gauss-Newton algorithm will be illustrated. To simply notation, the following are introduced:

$$x = (R_{SAD}, x_0, y_0, z_0, \theta, \phi, \alpha) \quad (11)$$

$$y_i = \frac{r_{sd}(\beta)_i}{\|r_{sd}\|} \quad (12)$$

$$r_{so}(R_{SAD}, \beta) = R_{SAD} \cdot (-\sin\beta, -\cos\beta, 0) \quad (13)$$

$$v(x) = r_{so}(R_{SAD}, \beta) + r_{oo'}(x_0, y_0, z_0) + r_{o'b}(\theta, \phi, \alpha) \quad (14)$$

$$u(x) = v \cdot v \quad (15)$$

$$F_i = \frac{v_i}{\sqrt{u(x)}} \quad (16)$$

where an appropriate indexing over both the vector components and the reference objects is understood. $R_{SAD}$ is the distance from the source, i.e. the X-ray source 51, to the axis through origin of the calibration tool 110, i.e. the position of the calibration tool 110. Next, the residuals $v_i$ are considered when solving equation (10):

$$v_i = y_i - F_i(x) \quad (17)$$

for which the Gauss-Newton algorithm strives to minimize the sum of squares. Starting with an initial guess $x^0$, the algorithm iteratively updates the solution according to:

$$x^{n+1} = x^n + \Delta \quad (18)$$

where $\Delta$ is a small step determined by solving the normal equations:

$$(J^T J)\Delta = J^T v \quad (19)$$

and J in turn is the Jacobian of F with respect to x, i.e.:

$$J_{ij}(x^n) = \left.\frac{\partial F_i}{\partial x_j}\right|_{x=x^n} \quad (20)$$

The normal equations may be solved in one step using Cholesky decomposition or QR factorization of J. For large systems, an iterative method, such as the conjugate gradient method, may be more efficient. Then, an analytical expression of J(x) can be computed:

$$J = \begin{pmatrix} \nabla F_1 \\ \nabla F_2 \\ \vdots \end{pmatrix} = \frac{\nabla v_i}{\sqrt{u}} - \frac{v_i}{2u^{3/2}} \cdot \nabla u \qquad (21)$$

Since $v(x) = r_{so}(R_{SAD}, \beta) + r_{oo'}(x_0, y_0, z_0) + r_{o'b}(\theta, \phi, \alpha)$, the following applies:

$$\frac{\partial v}{\partial R_{SAD}} = \frac{\partial r_{so}}{\partial R_{SAD}} = (-\sin\beta, -\cos\beta, 0) \qquad (22)$$

$$\frac{\partial v}{\partial x_0} = \frac{\partial r_{oo'}}{\partial x_0} = (1, 0, 0) \qquad (23)$$

$$\frac{\partial v}{\partial y_0} = \frac{\partial r_{oo'}}{\partial y_0} = (0, 1, 0) \qquad (24)$$

$$\frac{\partial v}{\partial z_0} = \frac{\partial r_{oo'}}{\partial z_0} = (0, 1, 0) \qquad (25)$$

$$\frac{\partial v}{\partial \theta} = \frac{\partial r_{o'b}}{\partial \theta} = \left(\frac{\partial \hat{k}}{\partial \theta} \times r_{o'b}\right)\sin\alpha + \left(\frac{\partial \hat{k}}{\partial \theta}\left(\hat{k} \cdot r_{o'b}\right) + \hat{k}\left(\frac{\partial \hat{k}}{\partial \theta} \cdot r_{o'b}\right)\right)(1 - \cos\alpha) \qquad (26)$$

$$\frac{\partial v}{\partial \phi} = \qquad (27)$$

$$\frac{\partial r_{o'b}}{\partial \phi} = \left(\frac{\partial \hat{k}}{\partial \phi} \times r_{o'b}\right)\sin\alpha + \left(\frac{\partial \hat{k}}{\partial \phi}\left(\hat{k} \cdot r_{o'b}\right) + \hat{k}\left(\frac{\partial \hat{k}}{\partial \phi} \cdot r_{o'b}\right)\right)(1 - \cos\alpha)$$

$$\frac{\partial v}{\partial \alpha} = \frac{\partial r_{o'b}}{\partial \alpha} = (\hat{k} \times r_{o'b})\cos\alpha + (\hat{k}(\hat{k} \cdot r_{o'b}) - r_{o'b})\sin\alpha \qquad (28)$$

where $$\frac{\partial \hat{k}}{\partial \theta} = (\cos\phi\cos\theta, \sin\phi\cos\theta, -\sin\theta) \qquad (29)$$

$$\frac{\partial \hat{k}}{\partial \phi} = (-\sin\phi\sin\theta, \cos\phi\sin\theta, 0) \qquad (30)$$

Finally, the following applies:

$$\nabla u = 2(v \cdot \nabla)v \qquad (31)$$

which in component form translates to $$\frac{\partial u}{\partial x_j} = 2\sum_{n=1}^{7} v_n \frac{\partial v_n}{\partial x_j} \qquad (32)$$

Accordingly, the equation (21) can be written as:

$$J = \frac{\nabla v_i}{\sqrt{u}} - \frac{v_i}{u^{\frac{3}{2}}}(v \cdot \nabla)v \qquad (33)$$

With reference now to FIG. 7, the general steps of an embodiment of the method according to the present invention for calibrating an imaging system 50 for capturing images of a patient in connection with treatment planning or treatment in a radiation therapy system will be described. The method may, for example, be performed in a system as described in FIG. 2.

A first step may be to perform a calibration of image quality parameters of the imaging system 50 including determining a rotational axis of the imaging system 50. Alternatively, if a calibration has been performed earlier, the imaging system 50 may not need a calibration and calibration data can be stored in a calibration file.

At step 210, an image scanning procedure is initiated and the releasably attached calibration tool 110 is irradiated using the radiation unit 51 of the imaging system 50.

At step 220, at least one two-dimensional image including cross-sectional representations of the reference objects 112 of the calibration tool 110 is captured using the detector 52 of the imaging system 50 during the image scanning procedure.

At step 230, the image coordinates $d_{xy}$ of the representation or projection of each reference object 112 is identified or determined in the captured images. As has been described above, a point for each object 112 is determined that represents its projection is determined. Due to the size of the objects 112, their projections will occupy regions in the images larger than a pixel and therefore it will be efficient to identify point that represents the central point. For example, thresholding can be used to separate the projections from the background. The reference objects 112 are arranged on the calibration tool 110 such that no projections overlap either horizontally or vertically. A summing in the non-overlapping direction and an identifying of contiguous nonzero regions are performed. This procedure is repeated in both directions for each of the segmented strips. The sought point can be found in the resulting region of interest. A center of mass calculation can for example be used for this purpose.

At step 240, a position of the origin o of the calibration tool 110 in relation to the imaging unit 51 or the vector $r_{so}$ between the imaging unit 51 and the origin o of the calibration tool is obtained. In embodiments of the present invention, the vector $r_{so}$ between the imaging unit 51 and the origin o of the calibration tool is calculated and in other embodiments of the present invention, the vector $r_{so}$ between the imaging unit 51 and the origin o of the calibration tool is predetermined.

At step 250, a transformation including a translational and rotational position difference between the position of the calibration tool 110 in the stereotactic coordinate system and a position of the calibration tool 110 in an imaging system coordinate system is calculated using, for example, the equations (1)-(33) described above. Generally, the calculation is based on the reference objects image coordinates $d_{xy}$, positions $r_{ob}$ of the reference objects 112 in the stereotactic coordinate system relative to an origin o of the calibration tool 110 and a position $r_{so}$ of the origin o of the calibration tool 110 relative to the imaging unit 51. If SAD is not predetermined, SAD is calculated at the same time as the transformation is calculated.

In a following step, the transformation that has been calculated can be used for calibrating the imaging system 50 in relation to the radiation therapy system 1.

Turning now to FIG. 8, steps of another embodiment of the method according to the present invention for calibrating an imaging system 50 for capturing images of a patient in connection with treatment planning or treatment in a radiation therapy system will be described. The method may, for example, be performed in a system as described in FIG. 2. A first step may be to perform a calibration of image quality parameters of the imaging system 50 including determining a rotational axis of the imaging system 50. Alternatively, if a calibration has been performed earlier, the imaging system 50 may not need a calibration and calibration data can be stored in a calibration file.

At step 310, an image scanning procedure is initiated and the releasably attached calibration tool 110 is irradiated using the radiation unit 51 of the imaging system 50.

At step 320, at least one two-dimensional image including cross-sectional representations of the reference objects 112 of the calibration tool 110 is captured using the detector 52 of the imaging system 50 during the image scanning procedure.

At step 330, the image coordinates $d_{xy}$ of the representation or projection of each reference object 112 is identified or determined in the captured images. As has been described above, a point for each object 112 is determined that represents its projection is determined. Due to the size of the objects 112, their projections will occupy regions in the images larger than a pixel and therefore it will be efficient to identify point that represents the central point. For example, thresholding can be used to separate the projections from the background. The reference objects 112 are arranged on the calibration tool 110 such that no projections overlap either horizontally or vertically, see FIG. 4. A summing in the non-overlapping direction and an identifying of contiguous nonzero regions are performed. This procedure is repeated in both directions as shown in FIG. 4 for each of the segmented strips. The sought point can be found in the resulting region of interest. A center of mass calculation can for example be used for this purpose.

At step 340, positions $r_{sd}$ of the reference objects 112 relative to the imaging unit 51 is determined or calculated based on the reference objects image coordinates $d_{xy}$ and a position $r_{sd}$ of the detector 52 relative to the imaging unit or X-ray source 51.

At step 350, a position of the origin o of the calibration tool 110 in relation to the imaging unit 51 is obtained or the vector $r_{so}$ between the imaging unit 51 and the origin o of the calibration tool. In embodiments of the present invention, the vector $r_{so}$ between the imaging unit 51 and the origin o of the calibration tool is calculated and, in other embodiments of the present invention, the vector $r_{so}$ between the imaging unit 51 and the origin o of the calibration tool is predetermined.

At step 360, a transformation including a translational and rotational position difference between the position of the calibration tool 110 in the stereotactic coordinate system and a position of the calibration tool 110 in an imaging system coordinate system is calculated using, for example, the equations (1)-(31) described above. Generally, the calculation is based on the positions $r_{sd}$ of the reference objects relative to the imaging unit 51, positions $r_{o'b}$ of the reference objects in the imaging coordinate system and a position $r_{so}$ of the origin o of the calibration tool 110 relative to the imaging unit 51. If SAD is not predetermined, SAD is calculated at the same time as the transformation is calculated. In a following step, the transformation that has been calculated can be used for calibrating the imaging system 50 in relation to the radiation therapy system 1.

Turning now to FIG. 9, steps of further embodiment of the method according to the present invention for calibrating an imaging system 50 for capturing images of a patient in connection with treatment planning or treatment in a radiation therapy system will be described. The method may, for example, be performed in a system as described in FIG. 2. A first step may be to perform a calibration of image quality parameters of the imaging system 50 including determining a rotational axis of the imaging system 50. Alternatively, if a calibration has been performed earlier, the imaging system 50 may not need a calibration and calibration data can be stored in a calibration file.

At step 410, an image scanning procedure is initiated and the releasably attached calibration tool 110 is irradiated using the radiation unit 51 of the imaging system 50.

At step 420, at least one two-dimensional image including cross-sectional representations of the reference objects 112 of the calibration tool 110 is captured using the detector 52 of the imaging system 50 during the image scanning procedure.

At step 430, the image coordinates $d_{xy}$ of the representation or projection of each reference object 112 is identified or determined in the captured images. As has been described above, a point for each object 112 is determined that represents its projection is determined. Due to the size of the objects 112, their projections will occupy regions in the images larger than a pixel and therefore it will be efficient to identify point that represents the central point. For example, thresholding can be used to separate the projections from the background. The reference objects 112 are arranged on the calibration tool 110 such that no projections overlap either horizontally or vertically, see FIG. 4. A summing in the non-overlapping direction and an identifying of contiguous nonzero regions are performed. This procedure is repeated in both directions as shown in FIG. 4 for each of the segmented strips. The sought point can be found in the resulting region of interest. A center of mass calculation can for example be used for this purpose.

At step 440, vectors $r_{sb}$ between the reference objects positions and the position of the imaging unit 51 are determined based on the respective reference objects image coordinates $d_{xy}$ and an assumption that the vectors $r_{sb}$ between the reference objects positions and the position of the imaging unit 51 are parallel, for respective reference objects 112, with vectors $r_{sd}$ between positions the reference objects image coordinates $d_{xy}$ and the imaging unit 51.

At step 450, a position of the origin o of the calibration tool 110 in relation to the imaging unit 51 is obtained or the vector $r_{so}$ between the imaging unit 51 and the origin o of the calibration tool. In embodiments of the present invention, the vector $r_{so}$ between the imaging unit 51 and the origin o of the calibration tool is calculated and, in other embodiments of the present invention, the vector $r_{so}$ between the imaging unit 51 and the origin o of the calibration tool is predetermined.

At step 460, a transformation including a translational and rotational position difference between the position of the calibration tool 110 in the stereotactic coordinate system and a position of the calibration tool 110 in an imaging system coordinate system is calculated using, for example, the equations (1)-(31) described above using also the relation between the vectors $r_{sd}$ between the reference objects positions and the position of the imaging unit 51 and the vectors $r_{sb}$ between positions the reference objects image coordinates $d_{xy}$ and the imaging unit 51 in calculating the transformation. If SAD is not predetermined, SAD is calculated at the same time as the transformation is calculated.

In a following step, the transformation that has been calculated can be used for calibrating the imaging system 50 in relation to the radiation therapy system 1.

Even though the present invention has been described above using exemplifying embodiments thereof, alterations, modifications, and combinations thereof, as understood by those skilled in the art, may be made without departing from the scope of the invention as defined in the accompanying claims.

The invention claimed is:

1. A method for calibrating an imaging system capturing images of a patient in relation to a radiation therapy system, which comprises a radiation therapy unit having a fixed radiation focus, and a positioning system configured to position the patient in relation to the fixed radiation focus in the radiation therapy unit, the method comprising steps of:

irradiating a calibration tool comprising a plurality of reference objects with ionizing radiation during an image scanning procedure using a radiation unit of the imaging system, wherein the calibration tool and the plurality of reference objects have known positions in a stereotactic coordinate system;

capturing at least one two-dimensional image including cross-sectional representations of the plurality of reference objects of the calibration tool using a detector of the imaging system during the image scanning procedure;

determining image coordinates, $d_{xy}$, of the cross-sectional representation of each of the plurality of reference objects in the captured at least one two-dimensional images;

obtaining a vector, $r_{so}$, from an origin or center point, o, of the calibration tool to an imaging unit in the stereotactic coordinate system and obtaining a vector $r_{o'b}$ from an origin, o', of the calibration tool in an imaging system coordinate system to each of the plurality of reference objects; and calculating a transformation between a 3D position of the calibration tool in the stereotactic coordinate system and a 3D position of the calibration tool in the imaging system coordinate system, wherein the calculation of the transformation uses the image coordinates, $d_{xy}$, a known vector, $r_{ob}$, from each of the plurality of reference objects in the stereotactic coordinate system to the origin, o, of the calibration tool in the stereotactic coordinate system, the vector, $r_{so}$, and a vector $r_{sb}$ from each of the plurality of reference objects to the imaging unit, and the vector $r_{sb}$ is calculated by $$r_{sb}=r_{so}+r_{ob}+=r_{so}+r_{o,o}+r_{o'b},$$

wherein $r_{o,o'}$ is a vector from the origin, o, of the calibration tool in the stereotactic coordinate system to the origin, o', of the calibration tool in the imaging system coordinate system; and determining a relation between coordinates or vectors in the stereotactic coordinate system and the imaging system coordinate system using a Rodrigues rotation formula for vector rotation in space.

2. The method according to claim 1, wherein the step of obtaining the vector, $r_{so}$, from the origin, o, of the calibration tool to the imaging unit includes calculating the vector, $r_{so}$, of the origin, o, of the calibration tool to the imaging unit.

3. The method according to claim 2, further comprising:

determining a vector, $r_{sd}$, from each of the plurality of reference objects to the imaging unit based on the image coordinates, $d_{xy}$, and a vector from the detector to the imaging unit; and calculating the transformation using a vector, $r_{sd}$, from each of the plurality of reference objects to the imaging unit, a vector, $r_{o'b}$, from each of the plurality of reference objects to the origin, o', of the calibration tool in the imaging system coordinate system, and a vector, $r_{so}$, from the calibration tool to the imaging unit.

4. The method according to claim 1, further comprising steps of:

determining vector, $r_{sd}$, from each of the plurality of reference objects to the imaging unit from the image coordinates, $d_{xy}$, and a vector from the detector to the imaging unit; and calculating the transformation using a vector, $r_{sd}$, from each of the plurality of reference objects relative to the imaging unit, vectors, $r_{o'b}$, from the plurality of reference objects to the origin, o', of the imaging system coordinate system, and a vector, $r_{so}$, from the calibration tool to the imaging unit.

5. The method according to claim 1, wherein the calculation of the transformation is further using a known source to detector distance, SDD, between the imaging unit and the detector and a detector rotation between a position of the detector in the stereotactic coordinate system and a position of the detector in the imaging system coordinate system.

6. The method according to claim 1, further comprising steps of:

determining vectors, $r_{sb}$, between the plurality of reference objects' positions and the position of the imaging unit based on the respective image coordinates, $d_{xy}$, given that the vectors, $r_{sb}$, between the plurality of reference objects' positions and the position of the imaging unit are parallel, for respective reference objects, with vectors between positions of the image coordinates, $d_{xy}$, and the imaging unit; and using the relation between vectors between the plurality of reference objects' positions and the position of the imaging unit and vectors between the positions of the image coordinates, $d_{xy}$, and the imaging unit in calculating the transformation.

7. The method according to claim 6, further comprising steps of:

defining the relation between vectors, $r_{sd}$, for the image coordinates, $d_{xy}$, relative to the imaging unit and the vectors, $r_{sb}$, of the plurality of reference objects' positions relative to the imaging unit as a scalar; and determining a value of the scalar based on a vector from each of the plurality of reference objects to the imaging unit, a vector, $r_{o'b}$, from each of the plurality of reference objects to the origin, o', of the imaging system coordinate system, and a vector, $r_{so}$, from the calibration tool to the imaging unit.

8. The method according to claim 1, further comprising steps of:

calculating vectors, $r_{o'b}$, from each of the plurality of reference objects to the origin, o, of the calibration tool in the imaging system coordinate system based on the vectors, $r_{ob}$, from each of the plurality of reference objects to the origin, o, of the calibration tool in the stereotactic coordinate system; and calculating the transformation using the image coordinates, $d_{xy}$, the coordinates, $r_{o'b}$, of the plurality of reference objects in the imaging system coordinate system and coordinates, $r_{so}$, of the calibration tool relative to the imaging unit.

9. The method according to claim 1, wherein each relation between coordinates of a position of a reference object of a plurality of reference objects in the stereotactic coordinate system and coordinates of a position of that reference object in the imaging system coordinate system is calculated as a vector defining a translational and rotational transformation using a vector-related method.

10. The method according to claim 1, wherein the positioning system includes a fixation arrangement configured to releasably and firmly engage a stereotactic fixation unit for immobilizing at least a part of the patient in relation to the positioning system.

11. A system for calibrating an imaging system for capturing images of a patient in relation to a radiation therapy system, which comprises a radiation therapy unit having a fixed radiation focus, and a positioning system configured to position the patient in relation to the fixed radiation focus in the radiation therapy unit, wherein:

the imaging system is configured to irradiate a calibration tool comprising a plurality of reference objects with ionizing radiation during an image scanning procedure using a radiation unit, wherein the calibration tool and the plurality of reference objects have known positions in a stereotactic coordinate system;

the imaging system is configured to capture at least one two-dimensional image including cross-sectional representations of the plurality of reference objects of the calibration tool using a detector during the image scanning procedure;

a processor is configured to: determine image coordinates, $d_{xy}$, of the cross-sectional representation of each reference object in the captured at least one two-dimensional images;

obtain a vector, $r_{so}$, from an origin or center point, o, of the calibration tool to an imaging unit in the stereotactic coordinate system and obtain a vector $r_{o'b}$ from an origin, o', of the calibration tool in the imaging system coordinate system to each of the plurality of reference objects; and calculate a transformation between a 3D position of the calibration tool in the stereotactic coordinate system and a 3D position of the calibration tool in an imaging system coordinate system, wherein the calculation of the transformation uses the image coordinates, $d_{xy}$, a known vector, $r_{ob}$, from each of the plurality of reference objects in the stereotactic coordinate system to the origin, o, of the calibration tool in the stereotactic coordinate system, the vector, $r_{so}$, and a vector $r_{sb}$ from each of the plurality of reference objects to the imaging unit, and the vector $r_{sb}$ is calculated by $$r_{sb} = r_{so} + r_{ob} = r_{so} + r_{oo'} + r_{o'b},$$

wherein $r_{oo'}$ is a vector from the origin, o, of the calibration tool in the stereotactic coordinate system to the origin, o', of the calibration tool in the imaging system coordinate system; and determine a relation between coordinates or vectors in the stereotactic coordinate system and the imaging system coordinate system using a Rodrigues rotation formula for vector rotation in space.

12. The system according to claim 11, wherein the processor is further configured to calculate the vector $r_{so}$ from the origin, o, of the calibration tool to the imaging unit.

13. The system according to claim 12, wherein the processor is further configured to:

determine a vector, $r_{sd}$, from each of the plurality of reference objects to the imaging unit based on the image coordinates, $d_{xy}$, and a a vector from the detector to the imaging unit; and calculate the transformation using a vector, $r_{sd}$, from each of the plurality of reference objects to the imaging unit, a vector, $r_{o'b}$, from each of the plurality of reference objects in the imaging system coordinate system, and a vector, $r_{so}$, from the calibration tool to the imaging unit.

14. The system according to claim 11, wherein the processor is further configured to:

determine a vector, $r_{sd}$, from each of the plurality of reference objects to the imaging unit based on the image coordinates, $d_{xy}$, and a vector from the detector to the imaging unit; and calculate the transformation based on a vector, $r_{sd}$, from each of the plurality of reference objects to the imaging unit, a vector, $r_{o'b}$, from each of the plurality of reference objects in the imaging system coordinate system, and a vector, $r_{so}$, from the calibration tool to the imaging unit.

15. The system according to claim 11, wherein the processor is further configured to calculate the transformation using a known source to detect distance, SDD, between the imaging unit and the detector and a detector rotation between a position of the detector in the stereotactic coordinate system and a position of the detector in the imaging system coordinate system.

16. The system according to claim 11, wherein the processor is Further configured to:

determine vectors, $r_{sb}$, between the plurality of reference objects' positions and the position of the imaging unit based on the respective image coordinates, $d_{xy}$, given that the vectors, $r_{sb}$, between the plurality of reference objects' positions and the position of the imaging unit are parallel, for respective reference objects, with vectors between positions of the image coordinates, $d_{xy}$, and the imaging unit; and using the relation between vectors between the plurality of reference objects' positions and the position of the imaging unit and vectors between the positions of the image coordinates, $d_{xy}$, and the imaging unit in calculating the transformation.

17. The system according to claim 16, wherein the processor is further configured to:

define the relation between vectors, $r_{sd}$, for the image coordinates, $d_{xy}$, relative to the imaging unit and the vectors, $r_{sb}$, of the plurality of reference objects' positions relative to the imaging unit as a scalar; and determine a value of the scalar based on a vector from each of the plurality of reference objects to the imaging unit, a vector, $r_{o'b}$, from each of the plurality of reference objects to the origin, o', of the imaging system coordinate system and a vector, $r_{so}$, from the calibration tool to the imaging unit.

18. The system according to claim 11, wherein the processor is further configured to:

calculate a vector, $r_{o'b}$, from each of the plurality of reference objects to the origin, o, of the calibration tool in the imaging system coordinate system based on the a vector, $r_{ob}$, from each of the plurality of reference objects to the origin, o, of the calibration tool in the stereotactic coordinate system; and calculate the transformation using the image coordinates, $d_{xy}$, the vector, $r_{o'b}$, of from each of the plurality of reference objects in the imaging system coordinate system and a vector, $r_{so}$, of the calibration tool relative to the imaging unit.

19. The system according to claim 11, wherein each relation between coordinates of a position of a reference object of a plurality of reference objects in the stereotactic coordinate system and coordinates of a position of that reference object in the imaging system coordinate system is calculated as a vector defining a translational and rotational transformation using a vector-related method.

20. The system according to claim 11, wherein the positioning system includes a fixation arrangement configured to releasably and firmly engage a stereotactic fixation unit for immobilizing at least a part the patient in relation to the positioning system.

\* \* \* \* \*